US012730800B2

(12) United States Patent
Bharatia et al.

(10) Patent No.: US 12,730,800 B2
(45) Date of Patent: Sep. 8, 2026

(54) SYSTEM AND METHOD FOR IMPLEMENTING INTELLIGENT SERVICE REQUEST REMEDY

(71) Applicant: CERNER INNOVATION, INC., North Kansas City, MO (US)

(72) Inventors: Chirag Bharatia, Bangalore (IN); Vijay Chendrayan Chandrasekar, Bengaluru (IN); Sundareshan M, Bengaluru (IN); Deepak Kumar Shivalingappa, Bengaluru (IN); Jerry George, Bengaluru (IN); Uma Akula, Bengaluru (IN)

(73) Assignee: CERNER INNOVATION, INC., Kansas City, MO (US)

( * ) Notice: Subject to any disclaimer, the term of this patent is extended or adjusted under 35 U.S.C. 154(b) by 1516 days.

(21) Appl. No.: 17/133,158

(22) Filed: Dec. 23, 2020

(65) Prior Publication Data

US 2022/0197898 A1 Jun. 23, 2022

(51) Int. Cl.

| | |
|---|---|
| ***G06F 16/242*** | (2019.01) |
| ***G06N 3/08*** | (2023.01) |
| ***G06N 20/00*** | (2019.01) |
| ***G10L 15/18*** | (2013.01) |
| ***G16H 10/60*** | (2018.01) |

(52) U.S. Cl.

CPC ............. *G06F 16/243* (2019.01); *G06N 3/08* (2013.01); *G06N 20/00* (2019.01); *G10L 15/18* (2013.01); *G16H 10/60* (2018.01)

(58) Field of Classification Search

CPC ..... G06F 16/243; G06F 40/279; G16H 10/60; G16H 40/67; G06N 20/00; G06N 3/08; G06N 5/01; G06N 20/20; G10L 15/18

See application file for complete search history.

(56) References Cited

U.S. PATENT DOCUMENTS

| | | | | |
|---|---|---|---|---|
| 2013/0111488 A1* | 5/2013 | Gatti | ...................... | G06N 20/10 718/103 |
| 2014/0149411 A1* | 5/2014 | Anand | .................... | G06F 16/35 707/737 |
| 2017/0140114 A1* | 5/2017 | Are | .......................... | G06N 5/01 |
| 2017/0372231 A1* | 12/2017 | Ghatage | ................. | G06F 40/58 |

(Continued)

OTHER PUBLICATIONS

Jugovac, Michael, and Dietmar Jannach. "Interacting with recommenders—overview and research directions." ACM Transactions on Interactive Intelligent Systems (TiiS) 7.3 (2017): 1-46. https://dl.acm.org/doi/abs/10.1145/3001837 (Year: 2017).*

*Primary Examiner* — Michael H Hoang

(74) *Attorney, Agent, or Firm* — Invoke

(57) ABSTRACT

Methods, systems, and computer-readable media are disclosed herein for intelligent service request analysis and remedy. In an aspect, a service request related to a computer system is received. Once received, natural language processing is conducted to determine at least one key term associated with the at least one service request. A machine learning algorithm is then used to determine at least one classification group for the at least one service request, wherein the classification group is associated with the remedy. A rate of success is determined for the determined remedy for the classification group. Based on the rate of success exceeding a predetermined threshold, cause the remedy to be implemented in the computer system.

20 Claims, 16 Drawing Sheets

(56) References Cited

U.S. PATENT DOCUMENTS

| | | | | |
|---|---|---|---|---|
| 2018/0121607 | A1* | 5/2018 | Bastide | G16H 10/60 |
| 2019/0244134 | A1* | 8/2019 | Midboe | H04L 67/535 |
| 2020/0202997 | A1* | 6/2020 | Hadad | G16H 50/70 |
| 2022/0012605 | A1* | 1/2022 | Purushothaman | G06N 5/022 |
| 2022/0076851 | A1* | 3/2022 | Kamangar | G06Q 30/0633 |
| 2022/0398664 | A1* | 12/2022 | Stensrud | G06Q 40/06 |

* cited by examiner

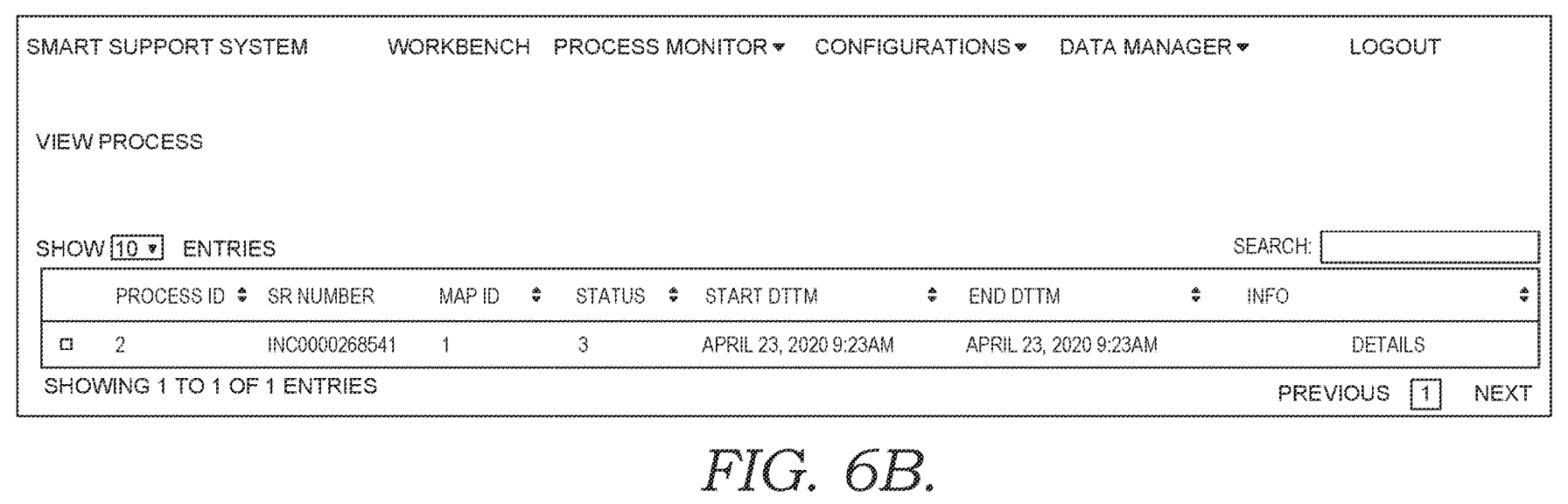

SMART SUPPORT SYSTEM WORKBENCH PROCESS MONITOR ▾ CONFIGURATIONS ▾ DATA MANAGER ▾ LOGOUT

VIEW PROCESS

SHOW 10 ▾ ENTRIES SEARCH:

| | PROCESS ID | SR NUMBER | MAP ID | STATUS | START DTTM | END DTTM | INFO |
|---|---|---|---|---|---|---|---|
| ☐ | 2 | INC0000268541 | 1 | 3 | APRIL 23, 2020 9:23AM | APRIL 23, 2020 9:23AM | DETAILS |

SHOWING 1 TO 1 OF 1 ENTRIES PREVIOUS 1 NEXT

*FIG. 6B.*

SMART SUPPORT SYSTEM WORKBENCH PROCESS MONITOR ▾ CONFIGURATIONS ▾ DATA MANAGER ▾ LOGOUT

RE-TRAIN MODEL

SHOW 10 ▾ ENTRIES SEARCH:

| SR NUMBER | SUMMARY | NOTES | MESSAGE | PRODUCT | STATUS | CLASS | SUB-CLASS | SUG. CLASS | SUG. SUB-CLASS |
|---|---|---|---|---|---|---|---|---|---|
| INC0000184302 | PLEASE PROVIDE ACCESS TO CHANGE MANAGEMENT CONSOLE TO WORK ON THE TICKETS IN REMEDY | | PLEASE PROVIDE ACCESS TO CHANGE MANAGEMENT CONSOLE TO WORK ON THE TICKETS IN REMEDY | REMEDY | | ACCESS | CHANGE MANAGEMENT CONSOLE | NONE | NONE |
| INC0000228807 | PLEASE PROVIDE ACCESS TO CHANGE MANAGEMENT CONSOLE TO WORK ON THE TICKETS IN REMEDY | | PLEASE PROVIDE ACCESS TO CHANGE MANAGEMENT CONSOLE TO WORK ON THE TICKETS IN REMEDY | REMEDY | | PAYROLL DEDUCTION | LUNCH DEDUCTION | NONE | NONE |

SHOWING 1 TO 2 OF 2 ENTRIES PREVIOUS 1 NEXT

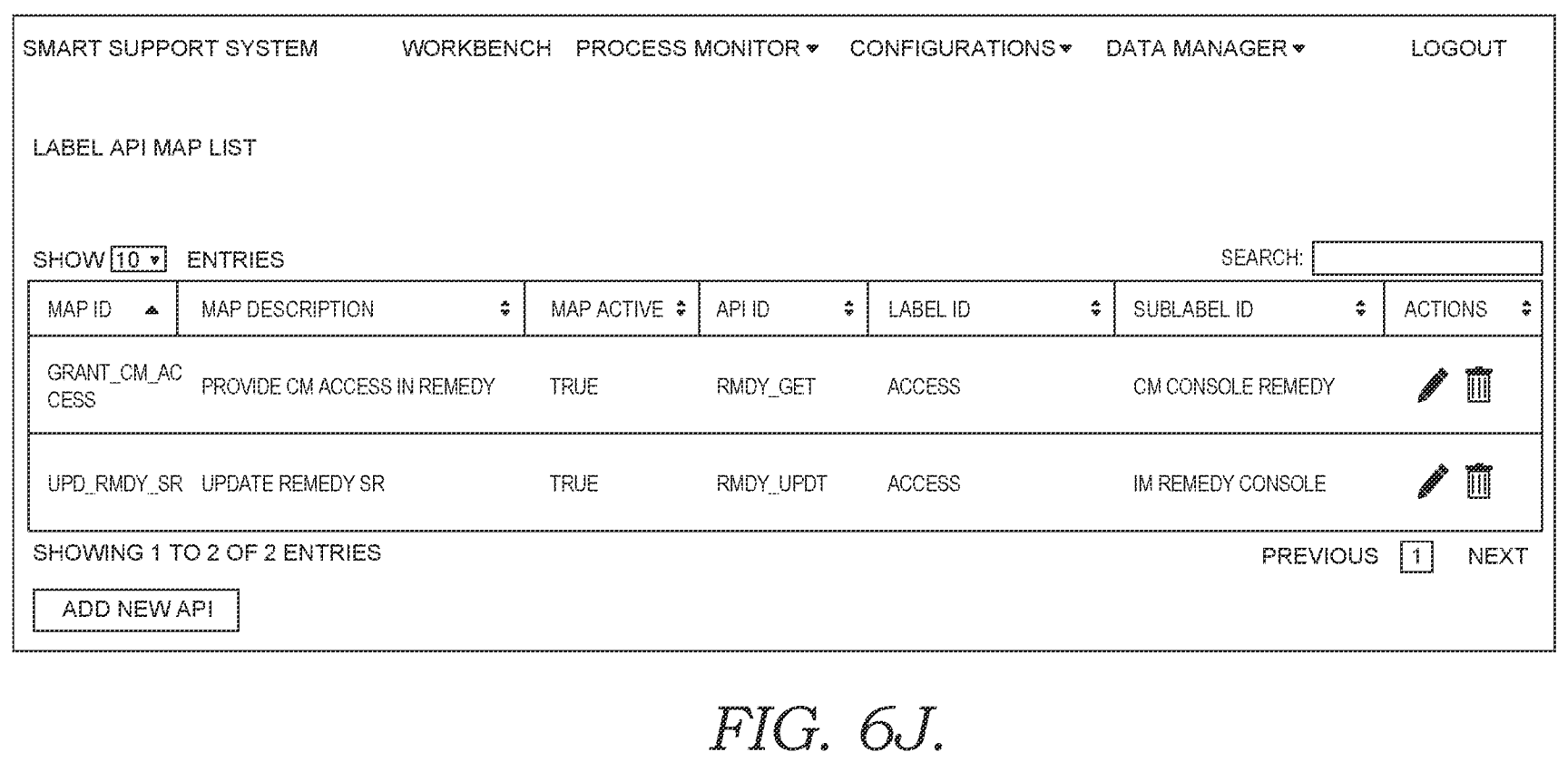

SMART SUPPORT SYSTEM WORKBENCH PROCESS MONITOR ▾ CONFIGURATIONS ▾ DATA MANAGER ▾ LOGOUT

LABEL API MAP LIST

SHOW 10 ▾ ENTRIES SEARCH:

| MAP ID | MAP DESCRIPTION | MAP ACTIVE | API ID | LABEL ID | SUBLABEL ID | ACTIONS |
|---|---|---|---|---|---|---|
| GRANT_CM_ACCESS | PROVIDE CM ACCESS IN REMEDY | TRUE | RMDY_GET | ACCESS | CM CONSOLE REMEDY | |
| UPD_RMDY_SR | UPDATE REMEDY SR | TRUE | RMDY_UPDT | ACCESS | IM REMEDY CONSOLE | |

SHOWING 1 TO 2 OF 2 ENTRIES PREVIOUS 1 NEXT

ADD NEW API

FIG. 6J.

SYSTEM AND METHOD FOR IMPLEMENTING INTELLIGENT SERVICE REQUEST REMEDY

BACKGROUND

Receiving and reviewing service request tickets is an integral part of the Information Technology (IT) process. As systems become more complicated and gain increasingly large numbers of users, the service requests received by IT engineers too become more complicated and increase in number. For instance if a server goes down for a midsized to large company, the IT engineers associated with that company may receive incredibly large numbers of service requests related to that issue. While the issue may not be overly complicated, IT engineers still must deal with each service request as they come in. At best, current service request analysis requires that IT engineers review each new service request ticket, determine the issue, and then determine a remedy for that issue. As IT engineers can receive incredible amounts of service requests per day, the current process can delay remedy of issues for extended periods of time.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description and Drawings.

In brief and at a high level, embodiments of the present invention provide systems, methods, and computer-readable media for intelligent remedy of computer system service requests. Embodiments provide an application and/or cloud-based service that intelligently implement remedies of computer system service requests. The remedy tool determines at least one classification group associated with a remedy. And, based on determining that a rate of success for the remedy is above a threshold, the remedy is implemented.

One aspect of the present disclosure relates to a method for implementing intelligent remedy of computer system service requests. In aspects, a service request related to a computer system is received. In aspects, the method further comprises conducting natural language processing to determine at least one key term associated with the at least one service request. A machine learning algorithm is used to determine at least one classification group for the at least one service request, wherein the classification group is associated with at least one remedy. In aspects, based on the rate of success for the determined remedy for the classification exceeding a predetermined threshold, cause the computer system to implement the remedy.

In another aspect, the present disclosure relates to non-transitory computer-storage media having computer-executable instructions embodied thereon that, when executed, perform a method of implementing intelligent remedy of system service requests. In aspects, method comprises receiving at least one service request related to a system. Natural language processing is conducted to determine at least one key term associated with the at least one service request. In aspects, a machine learning algorithm is used to determine at least one classification group for the at least one service request, wherein the classification group is associated with at least one remedy. A rate of success for the determined remedy for the classification group is determined. In further aspects, the system is caused to implement the remedy based on the rate of success In yet another aspect, the present disclosure relates to a system for implementing intelligent remedy of system service requests. The system includes, a hardware processor configured to perform operations in response to receiving an instruction selected from a predefined native instruction set of codes, a memory, and a service request database configured to store at least one received service request related to a system. In further aspects, the system incudes, a processing component configured to: conduct natural language processing to determine at least one key term associated with the at least one service request. The processing component is further configured to determine at least one classification group for the at least one service request, wherein the classification group is associated with at least one remedy. In further aspects, the system also comprises a determination component configured to determine the rate of success for the at least one remedy for the classification group. In further aspects, the system also comprises, an implementation component configured to cause the system to implement the remedy, based on the rate of success exceeding a predetermined threshold.

BRIEF DESCRIPTION OF THE DRAWINGS

Embodiments are described in detail below with reference to the attached drawings figures, wherein:

FIGS. 6A-6J illustrate a plurality of graphical user interfaces that are responsive to user interactions with a graphical user interface, in accordance with embodiments of the present disclosure.

DETAILED DESCRIPTION

Figure 1A:
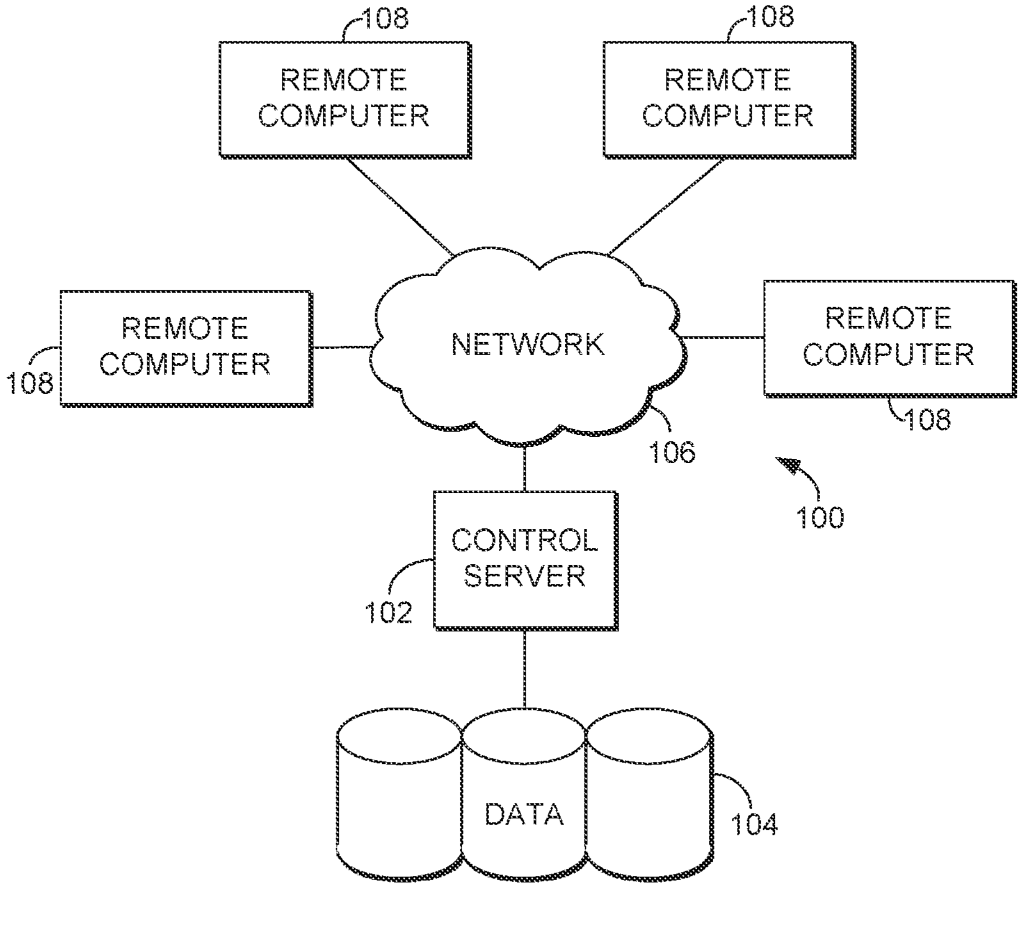
FIGS. 1A and 1B depict an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the disclosure may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-useable instructions embodied on one or more computer-readable media, as discussed further herein.

At a high level, embodiments of the present invention provide a system, computer-readable media, and methods for implementation of intelligent remedy of system service requests. The software product can communicate with one or more disparate sources to, among other things, access data from, for example, a system, receive system service requests, analyze one or more service requests, implement one or more determined remedies, and the like. The software product can provide the integration with a system while preserving privacy of an individual and the data associated therewith accessed from the system.

Embodiments herein provide a technological solution that addresses, solves, and overcomes the technological problems and/or shortcomings found in other systems which attempt to address service requests. The solution described herein intelligently analyzes service requests received from users of a system. As the amount of users of systems grow, so do the number of service requests received by an engineer related to defects or issues with those systems. If an engineer is required to manually sift through each and every one of these service requests, defects or issues may remain in existence for extended periods of times. These documented but unresolved issues can bog down not only the systems due to their related unresolved issues, but keep support staff from being able to resolve other issues. Additionally, increasing the speed by which service requests are dealt with, frees up storage space of the engineer computing system. As the issues are resolved quicker and without the need for review, the system does not need to dedicate computing power and memory space to these issues and service requests.

A computing environment is described with regard to the systems, methods, and computer-media described hereinabove. Turning to FIG. 1A, one example of a computing environment 100 is depicted, in accordance with an embodiment of the present invention. It will be understood by those of ordinary skill in the art that the computing environment 100 is just one example of a suitable computing environment and is not intended to limit the scope of use or functionality of the present invention. Similarly, the computing environment 100 should not be interpreted as imputing any dependency and/or any requirements with regard to each component and combination(s) of components illustrated in FIG. 1A. It will be appreciated by those having ordinary skill in the art that the connections illustrated in FIG. 1A are also exemplary as other methods, hardware, software, and devices for establishing a communications link between the components, devices, systems, and entities, as shown in FIG. 1A, may be utilized in implementation of the present invention. Although the connections are depicted using one or more solid lines, it will be understood by those having ordinary skill in the art that the connections of FIG. 1A may be hardwired or wireless, and may use intermediary components that have been omitted or not included in FIG. 1A for simplicity's sake. As such, the absence of components from FIG. 1A should be not be interpreted as limiting the present invention to exclude additional components and combination(s) of components. Moreover, though devices and components are represented in FIG. 1A as singular devices and components, it will be appreciated that some embodiments may include a plurality of the devices and components such that FIG. 1A should not be considered as limiting the number of a device or component.

Continuing, the computing environment 100 of FIG. 1A is illustrated as being a distributed environment where components and devices may be remote from one another and may perform separate tasks. The components and devices may communicate with one another and may be linked to each other using a network 106. The network 106 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 106, generally, provides the components and devices access to the Internet and web-based applications.

The computing environment 100 comprises a computing device 102 shown in the form of a server. Although illustrated as one component in FIG. 1A, the present invention may utilize a plurality of local servers and/or remote servers in the computing environment 100. The computing device 102 may include components such as a processing unit, internal system memory, and a suitable system bus 110 for coupling to various components, including a data store, database, or data store/database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing device 102 may include or may have access to computer-readable media. Computer-readable media can be any available media that may be accessed by computing device 102, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the computing device 102. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the computing device 102 uses logical connections to communicate with one or more remote computers 108 within the computing environment 100. In embodiments where the network 106 includes a wireless network, the computing device 102 may employ a modem to establish communications with the Internet, the computing device 102 may connect to the Internet using Wi-Fi or wireless access points, or the server may use a wireless network adapter to access the Internet. The computing device 102 engages in two-way communication with any or all of the components and devices illustrated in FIG. 1A, using the network 106. Accordingly, the computing device 102 may send data to and receive data from the remote computers 108 over the network 106.

Although illustrated as a single device, the remote computers 108 may include multiple computing devices. In an embodiment having a distributed network, the remote computers 108 may be located at one or more different geographic locations. In an embodiment where the remote computers 108 is a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computers 108 is physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. In other embodiments, the remote computers 108 may be physically located in a non-medical setting, such as a packing and shipping facility or deployed within a fleet of delivery or courier vehicles.

Continuing, the computing environment 100 includes a data store 104. Although shown as a single component, the data store 104 may be implemented using multiple data stores that are communicatively coupled to one another, independent of the geographic or physical location of a memory device. Exemplary data stores may store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. Exemplary data stores may also store data in the form of electronic records, for example, electronic medical records of patients, transaction records, billing records, task and workflow records, chronological event records, and the like.

Generally, the data store 104 includes physical memory that is configured to store information encoded in data. For example, the data store 104 may provide storage for computer-readable instructions, computer-executable instructions, data structures, data arrays, computer programs, applications, and other data that supports the functions and action to be undertaken using the computing environment 100 and components shown in exemplary FIG. 1A.

In various embodiments, the computing device 102, the one or more remote computers 108, and/or the data store 104 may be "sources" or "source devices," terms that are used interchangeably hereinafter. A source device can comprise any type of computing device capable of use by a user. By way of example and not limitation, a source device can be embodied as a personal computer (PC), a laptop computer, a mobile device, a smartphone, a tablet computer, a smart watch, a wearable computer, a fitness tracker, a personal digital assistant (PDA) device, a global positioning system (GPS) device, a video player, a handheld communications device, an embedded system controller, a camera, a remote control, a wearable electronic device with a camera (e.g., smart glasses, gesture-based wearable computers, etc.) a consumer electronic device, a workstation, or any combination of these delineated devices, a combination of these devices, or any other suitable computer device. The source device, as applied herein, can be utilized to access, for instance, the cloud-based solution to request creation of the item.

Additionally, the source devices can include clinical notes, appointment notes, records of issued prescriptions, diagnoses, care plans, bloodwork, urinalysis, treatment data, emergency contact information, and the like, for each patient of a healthcare facility or a plurality of healthcare facilities. Further, source devices can include images, representations, or clinical documentation of physical health data (e.g., X-rays, CT scans, ultrasound images, etc.). Additionally, in some embodiments, source devices can maintain one or more pharmaceutical formularies that identify prescriptions prescribed by, or available for prescription by, care providers.

In a computing environment having distributed components that are communicatively coupled via the network 106, program modules may be located in local and/or remote computer storage media including, for example only, memory storage devices. Embodiments of the present invention may be described in the context of computer-executable instructions, such as program modules, being executed by a computing device. Program modules may include, but are not limited to, routines, programs, objects, components, and data structures that perform particular tasks or implement particular abstract data types. In embodiments, the computing device 102 may access, retrieve, communicate, receive, and update information stored in the data store 104, including program modules. Accordingly, the computing device 102 may execute, using a processor, computer instructions stored in the data store 104 in order to perform embodiments described herein.

Although internal components of the devices in FIG. 1A, such as the computing device 102, are not illustrated, those of ordinary skill in the art will appreciate that internal components and their interconnection are present in the devices of FIG. 1A. Accordingly, additional details concerning the internal construction device are not further disclosed herein.

It should also be understood that the computing environment 100 shown in FIG. 1A is an example of one suitable computing system architecture. Each of the components of FIG. 1A may be implemented via any type of computing device. The components can communicate with each other via a network including, without limitation, one or more local area networks (LANs) and/or wide area networks (WANs). Such networking environments are commonplace in offices, enterprise-wide computer networks, intranets, and the Internet. It should be understood that any number of components shown in FIG. 1A may be employed within the computing environment 100 within the scope of the present invention. Each may be implemented via a single device or multiple devices cooperating in a distributed environment. Additionally, other components not shown may also be included within the environment. As such, it should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Figure 1B:
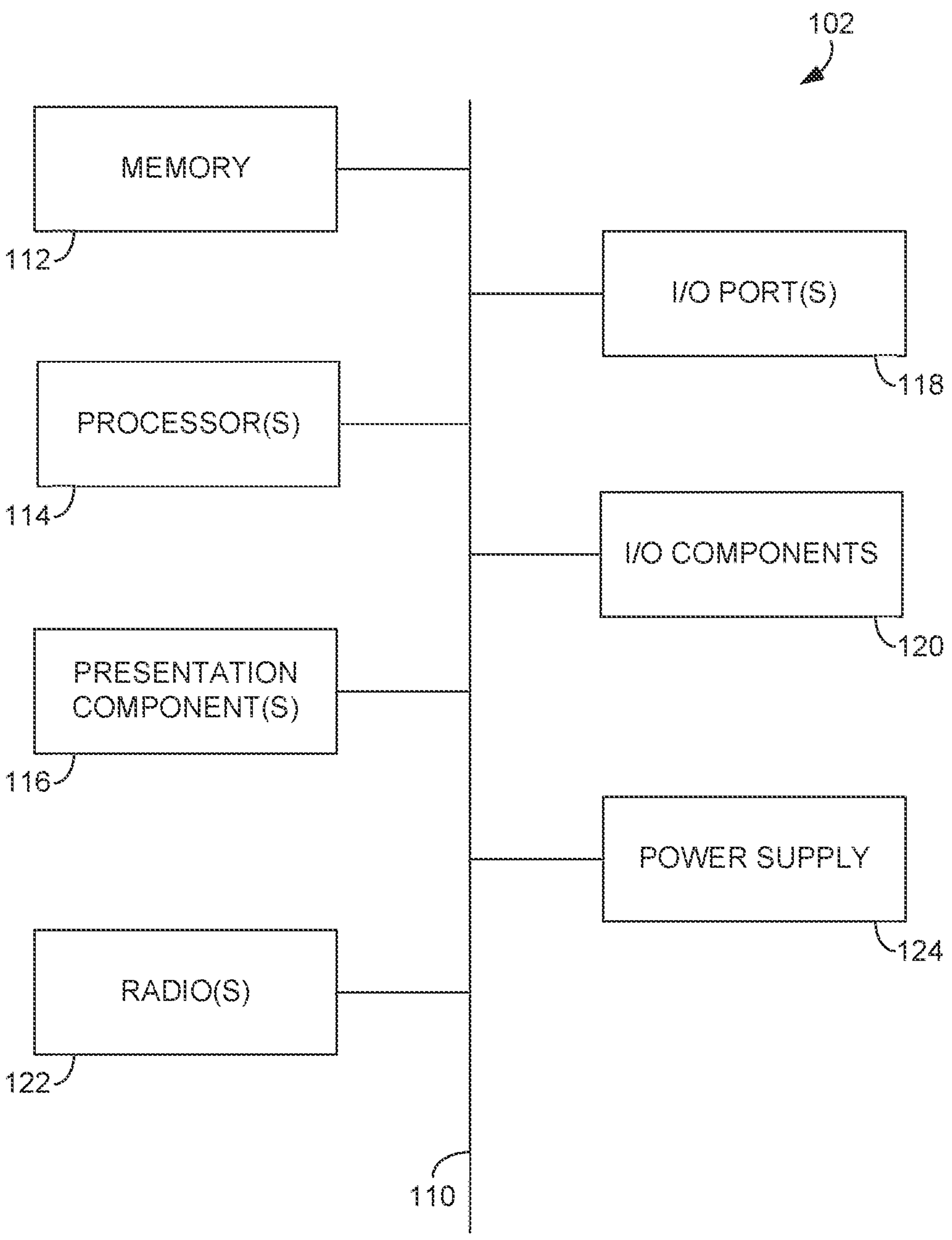

Turning to FIG. 1B, there is shown one example embodiment of the computing device 102. The computing device 102 includes a bus 110 that directly or indirectly couples one or more of the following components: memory 112, one or more processors 114, one or more presentation components 116, input/output (I/O) ports 118, input/output components 120, radio 122, and an illustrative power supply 124. Bus 110 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider the presentation components 116 to be an I/O component. Also, the one or more processors 114 may be couple to and/or be integrated with the memory 112. As such, the diagram of FIG. 1B is merely one example of the computing device 102 that can be used in connection with one or more embodiments of the present invention. Distinction is not made between such categories as "workstation," "server," "laptop," "hand-held device," etc., as all are contemplated within the scope of FIG. 1B and reference to "computing device."

The computing device 102 includes a variety of computer-readable media, in embodiments. Computer-readable media can be any available media that can be accessed by the computing device 102 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 112 includes computer-storage media in the form of volatile and/or nonvolatile memory. The memory 112 may be removable, non-removable, or a combination thereof. Examples of hardware components for memory include solid-state memory, hard drives, optical-disc drives, etc. The computing device 102 may include the one or more processors 114 that read data from the memory 112 and/or the I/O components 120. The presentation component(s) 116 present data indications to a user or other device. An example of the presentation component(s) 116 include a display device, speaker, printing component, vibrating component, etc.

In some embodiments, the computing device 102 may include one or more radio(s) 122 that facilitates communication with a wireless network. Illustrative wireless telecommunications technologies include CDMA, GPRS, TDMA, GSM, and the like, though embodiments are not limited to telecommunications networks. The radio(s) 122 may additionally or alternatively facilitate other types of wireless communications including Wi-Fi, WiMAX, LTE, or other VoIP communications. As can be appreciated, in various embodiments, the one or more radio(s) 122 can be configured to support multiple technologies and/or multiple radios can be utilized to support multiple technologies.

I/O ports 118 allow the computing device 102 to be logically coupled to other components, including I/O components 120, some of which may be built in to the computing device 102. Illustrative components include a microphone, joystick, game pad, satellite dish, scanner, printer, wireless device, etc. The I/O components 120 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 102. The computing device 102 may be equipped with depth cameras, such as stereoscopic camera systems, infrared camera systems, RGB camera systems, touchscreen technology, and combinations of these, for gesture detection and recognition. Additionally, the computing device 102 may be equipped with accelerometers or gyroscopes that enable detection of motion. Finally, the computing device 102 depicted in FIG. 1B is provided as one example of any number of suitable computers.

The computing device 102 may actually be a plurality of computing devices, in some embodiments. In various embodiments, the computing device 102 may include one or more software agents, an adaptive multi-agent operating system, or the like. It will be appreciated that the computing device 102 may take the form of an adaptive single agent system or a non-agent system, for example. The computing device 102 may be a distributed computing system of multiple remote computers, a data processing system, a centralized computing system, a networked computing system, or alternatively, may be a single computer such as a desktop or laptop computer.

Figure 2:
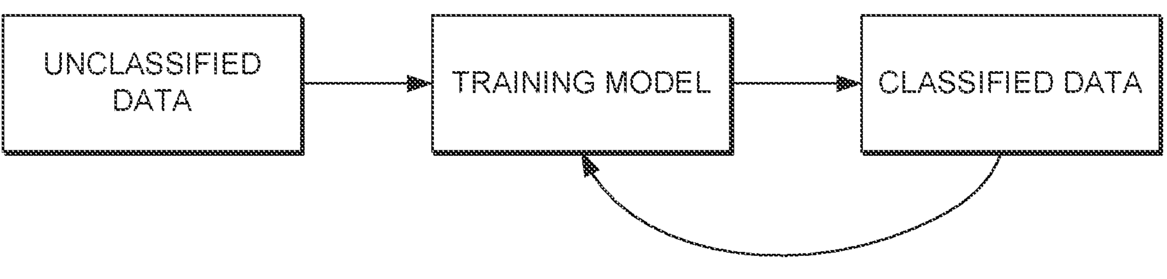
FIG. 2 illustrates a block diagram of a machine learning training model.

Turning to FIG. 2, an exemplary training model is provided for classifying data associated with service requests. In one embodiment, service requests are received from employees or associates within an organization. In another embodiment, service requests are receive by a service from one or more third parties, such as clients and users of an electronic medical record (EMR) system, such as Cerner Millennium®. In embodiments, the training model is populated with classified data. In example embodiments, the original training data is manually classified. In further embodiments, unclassified data is then provided to the training model which either successfully or unsuccessfully classifies the data. If the data is successfully classified, it is added back into the training model to aid the system in classifying future data. In example embodiments, if the data is unsuccessfully classified, it is flagged for retraining. In further embodiments, the classified data is assigned a success rate. If classified data is assigned a success rate under a predetermined threshold, it is flagged for review such that a user may review the classified data to ensure that it is appropriately classified. If it was successful, the data is added back into the training model as is. If unsuccessful, the data is manually classified and then added back into the training model.

In some embodiments, a random-forest based learning model may be used, which operates by constructing a multitude of decision trees, evaluating the features by using the decision trees, and sampling a set of data from features as a training set. The decision trees starts with a root node representing a parameter, for example, "use of the term 'access' or not". The decision tree can continue to grow with additional parameters. For example, under each decision tree, the decision tree will grow or be traversed based on additional nodes within the decision tree with additional parameters such as "use of the term 'locked out' or not" and "amount of time without access >15 minutes or not" wherein the amount of time without access is determined based on information from the application and information provided in the service request, or associated service requests. Each node with a parameter or test would represent a binary split or Boolean value where the features could be labeled as or associated with "Yes" (i.e., TRUE) or "No" (i.e. FALSE) for the particular node with the parameter or test. If input for a node is not selected from the results of any other node, then the node is defined as the top layer. If a node is selected from the results produced from an operation performed at a different node, the two nodes are in two different layers. In each layer, there might be a number of different nodes. In some embodiments, the parameters or tests used in nodes are randomly selected from a set of pre-defined parameters. The pre-defined parameters may be manually inputted into the machine learning system. In some embodiments, the features fed into one decision tree are a set of features that are associated with one user. In some embodiments, if the key terms determined from the service request include terms such as "unable to," "access," "application," the service request may be classified into the ACCESS classification group. At each node of the decision tree, preliminary categorization may be generated. Note that this preliminary categorization is a categorization used within in the learning model and may not be equivalent to the final output of the model.

In some embodiments, the preliminary results from each node of decision tree will be assigned a weight. The weight reflects how important that particular preliminary result is for the learning model. The decision tree can grow deeper indefinitely by incorporating additional nodes with parameters that relates to the features extracted from the system. For example, in one embodiment, the decision tree has four layers (in another words, the decision tree has a depth of four). The parameters used in the decision tree may be based on any feature extracted from the system. For example, a decision tree can use parameters that comprise key terms determined through natural language processing, or metadata associated with the received service request. Any number of key terms or amount of metadata may be used.

Figure 3:
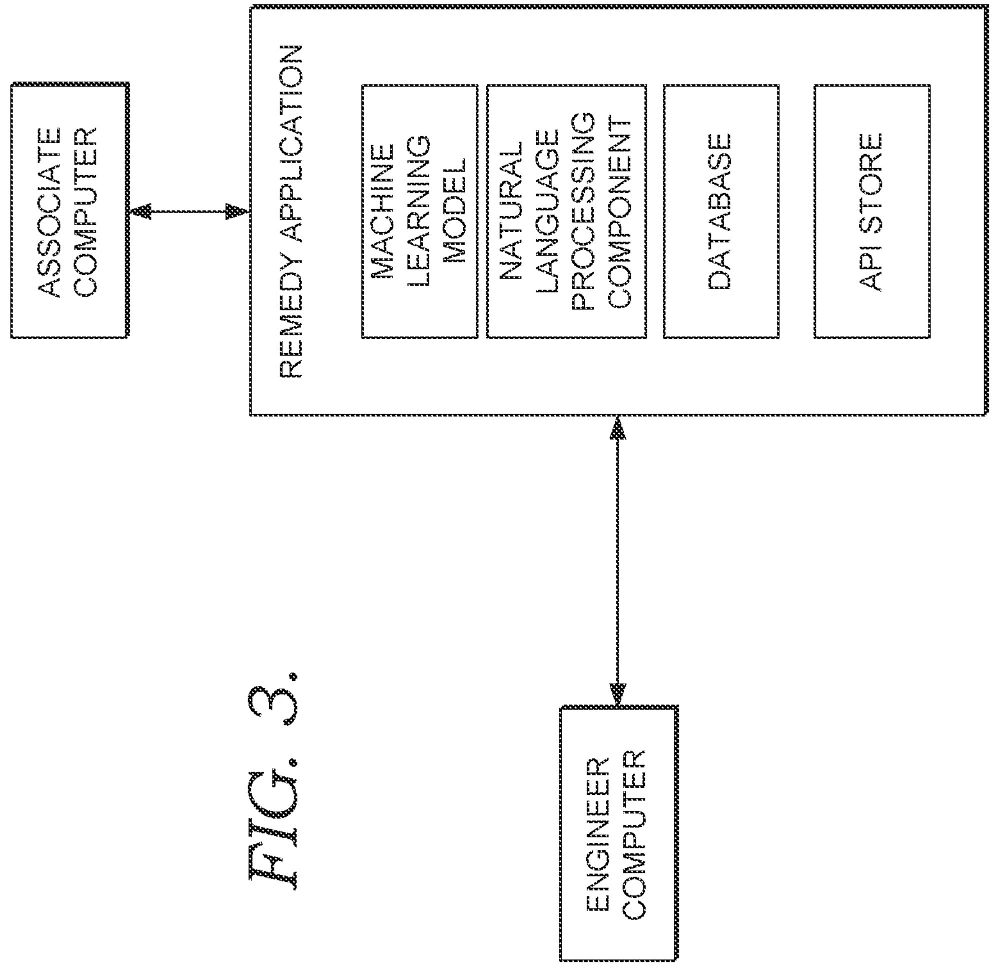
FIG. 3 illustrates a system environment for an exemplary embodiment for implementing intelligent remedy of system service requests, in accordance with an embodiment of the present disclosure.

FIG. 3, illustrates a system environment for an exemplary embodiment for implementing intelligent remedy of service requests, in accordance with an embodiment of the present disclosure. In example embodiments, the system is comprised of at least an engineer computer, an associate computer, and a Remedy Application. The Remedy Application contains at least a machine learning model, a natural language processing component, a database, and an Application Programming Interface (API) Store. Additionally, in exemplary embodiments, the Remedy Application is in communication with at least the engineer computer and the associated computer. In further embodiments, the engineer computer is configured to communicate with the Remedy Application. As shown in FIGS. 6A-6J, an engineer associated with the engineer computer may use a graphical user interface to customize the remedy application by creating labels associated with classification groups, sublabels associated with at least one classification subgroup, and at least one API. Additionally, the engineer associated with the engineer computer may create and customize associations between the APIs, labels, and sublabels. In further embodiments, if a determined classification group for a service request has a rate of success below a predetermined threshold, the Remedy Application can cause display of information associated with the determined label of a particular service request on a graphical user interface of the engineer computer. In further embodiments, if a determined classification group for a service request has a rate of success above a predetermined threshold, the Remedy Application causes the implementation of an associated remedy on the associate computer. In this embodiment, the information associated with the determined label is not displayed on the graphical user interface of the engineer computer. Therefore, in the exemplary embodiment displayed in FIG. 3, the Remedy Application may automatically cause remedy of a service request associated with an associate computer without further interaction by a second user, if the rate of success is above a predetermined threshold.

Figure 4:
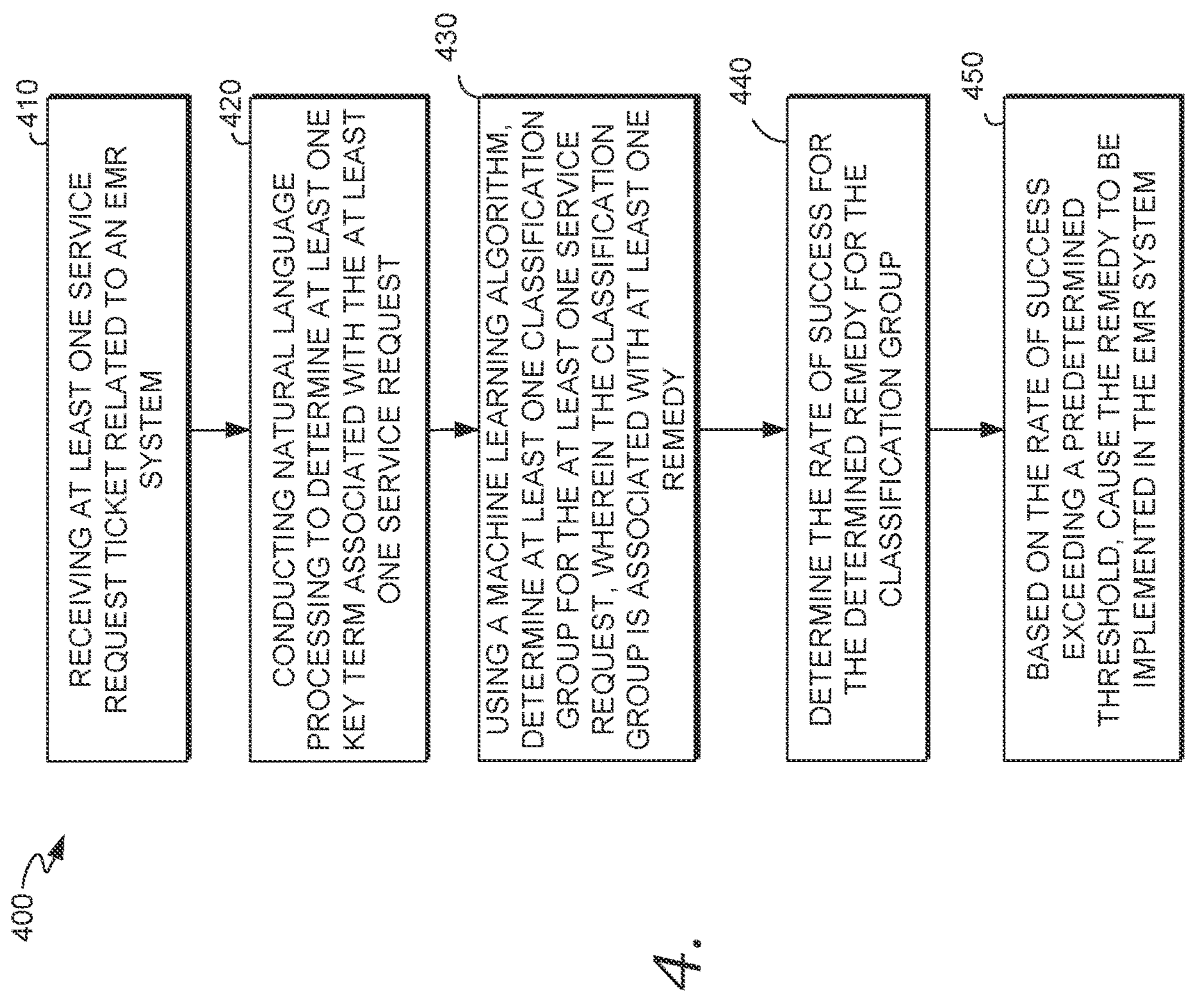
FIG. 4 illustrates a flow diagram of a method for implementing intelligent remedy of a system service requests, in accordance with an embodiment of the present disclosure.

Turning to FIG. 4, a flow diagram for a computer-implemented method for implementing intelligent remedy of a computer system service request is presented, in accordance with an embodiment of the present disclosure. The flow diagram of FIG. 4 also displays one or more non-transitory computer-storage media having computer-executable instructions embodied thereon that, when executed, perform a method for implementing intelligent remedy of system service requests. In example embodiments, a service request related to a computer system is received. As used herein, in embodiments, a service request is comprised of a digital file including information indicating a problem associated with a computer system. This digital file can be comprised of a text document, audio file, or other form of digital media. In further embodiments, the service request is related to a specific application associated with a computer system. In example embodiments, the applications can be associated with various aspects of a computer system, for example, data storage systems, email systems, accounting software, or database query software. In further embodiments, the received service requests are stored in a databased associated with the Remedy Application as shown in FIG. 3.

In further embodiments, the method includes conducting natural language processing to determine at least one key term associated with the at least one service request. In example embodiments, the natural language processing determines key words and phrases associated with the service request. This natural language processing can be conducted automatically, meaning as soon as the service request is received, the method would immediately implement the natural language processing. In further embodiments, the service request may be stored, in association with the data determined by the natural language processing, in a database associated with a computer system. In example embodiments, the natural language processing can be performed on service requests whether they are comprised of visual, textual, or audio data.

In further embodiments, once the natural language processing has been completed, the method further comprises using a machine learning algorithm to determine at least one classification group for the at least one service request, wherein the classification group is associated with at least one remedy. In example embodiments, a random forest algorithm may be used to determine the appropriate classification group, and in further embodiments, machine learning algorithm such as a deep neural network may be used. As described in association with FIG. 2, the determined classification groups may be stored in association with the service request and returned to the training model to further facilitate the sophistication of the training model. In further embodiments, the machine learning algorithm may take into account metadata associated with the service request, such as the identity of the user submitting the request, the application with which the request is associated, or information regarding other requests submitted by the user.

In further embodiments, the machine learning algorithm may also be used to determine at least one classification subgroup. These subgroups may be used to further specialize the classification group determined for the service request. In example embodiments, the groups and subgroups may be predefined by an engineer as described in association with FIG. 6 below. These predefined groups may be associated with any number of issues or technical difficulties associated with an system including at least one of an access issue, an update issue, an email issue, or a payroll issue. For example, the classification groups may be predefined with the label “ACCESS,” “PAYROLL DEDUCTION,” “EMAIL,” etc. An engineer could further define the classification group by predefining classification subgroups. For example, an engineer could predefine the subgroup having sublabel “CHANGE MANAGEMENT CONSOLE” to the classification group having label “ACCESS”, or predefine the subgroup having sublabel “LUNCH DEDUCTION” to the classification group having label “PAYROLL DEDUCTION.”

In further embodiments, the classification group, or classification subgroup is associated with at least one remedy. In example embodiments, this remedy may be predefined by an engineer via a graphical user interface as shown in FIG. 6. In further embodiments, the remedy is implemented using an Application Programming Interface (API). In example embodiments, the API is predefined by an engineer as shown, for example, in FIG. 6. In further embodiments, the predefined API is configured to implement a remedy associated with a classification group, or classification subgroup. For example, through the use of the graphical user interface displayed in FIG. 6, an engineer may customize the predefined API including creating and assigning endpoints which the API can access to carry out the remedy. Once predetermined and customized, the APIs may be mapped to predefined classification groups and classification subgroups. As shown, for example in FIG. 6J, an engineer may create predefined API Maps, or edit predefined API Maps. In example embodiments, the API Maps associate a specific API, or remedy, with a specific label or sublabel. Therefore, if the machine learning algorithm determines a classification group or classification subgroup for a service request, the associated API, or remedy, may be implemented.

In further embodiments, a rate of success for the determined remedy for the classification group is determined. In example embodiments, the determined rate of success may be associated with the classification group, classification subgroup, or both. In example embodiments, the rate of success may be determined based on the number of accurately classified groups or subgroups re-entered into the training model as shown in FIG. 2. In further embodiments, the threshold rate of success may be predetermined by an engineer, and this predetermined threshold may be customized for each group or subgroup.

In further embodiments, based on determining the rate of success exceeds a predetermined threshold, the remedy is implemented. In example embodiments, the remedy is automatically implemented using at least one API. As discussed above and below, this API may be preconfigured by an engineer and mapped to a classification group or classification subgroup. For example, if a determined classification group having label “PAYROLL DEDUCTION” with a determined classification subgroup having label “LUNCH DEDUCTION,” an API may be configured to remedy this issue. In further embodiments, the API may be configured to update the payroll account of a user associated with the submitted service request. In further embodiments, the API is configured to make use of a web server to automatically implement on the user computer associated with the service request.

For example, if a determined classification group having label “SERVER” is determined, the remedy associate with this issue may involve the system automatically implementing an API. This API may be pre-configured to access a server associated with a computer system. It is then determined that the server is down, and based on determining that the server associated with the system is down, a reboot of the server is caused. In an additional example, if a determined classification group having label “PAYROLL,” and classification subgroup having label “DEDUCTION”, the method may include automatically implementing a remedy associated with the classification group and subgroup combination. The remedy may be pre-configured to determine that a payroll system associated with a computer system has not processed a payroll deduction associated with a user of the computer system. Then, based on determining that the payroll system has not processed the payroll deduction, the payroll system is caused to process the payroll deduction.

In further embodiments, any combination of classification group and classification subgroup may have a remedy associated with that specific combination. For example a classification group label and classification subgroup label combination of "ACCESS" and "PROXY", or "ACCOUNT" and "MODIF", or "CAPACITY" and "ADD" may each have different preconfigured remedies associated with their classification label, and classification sublabel combination. For example the remedy associated with the combination of ACCESS and PROXY may be an API configured to determine that a user does not have access to a proxy system, and based on this determination, may provide access to that user. A different combination such as ACCOUNT and MODIFY, may have an associated remedy which modifies the account of a user by updating passwords, allowing third party access, or any number of other account actions. As such the system is not limited in the number of remedies and the classification group or classification subgroup associations.

Figure 6A:
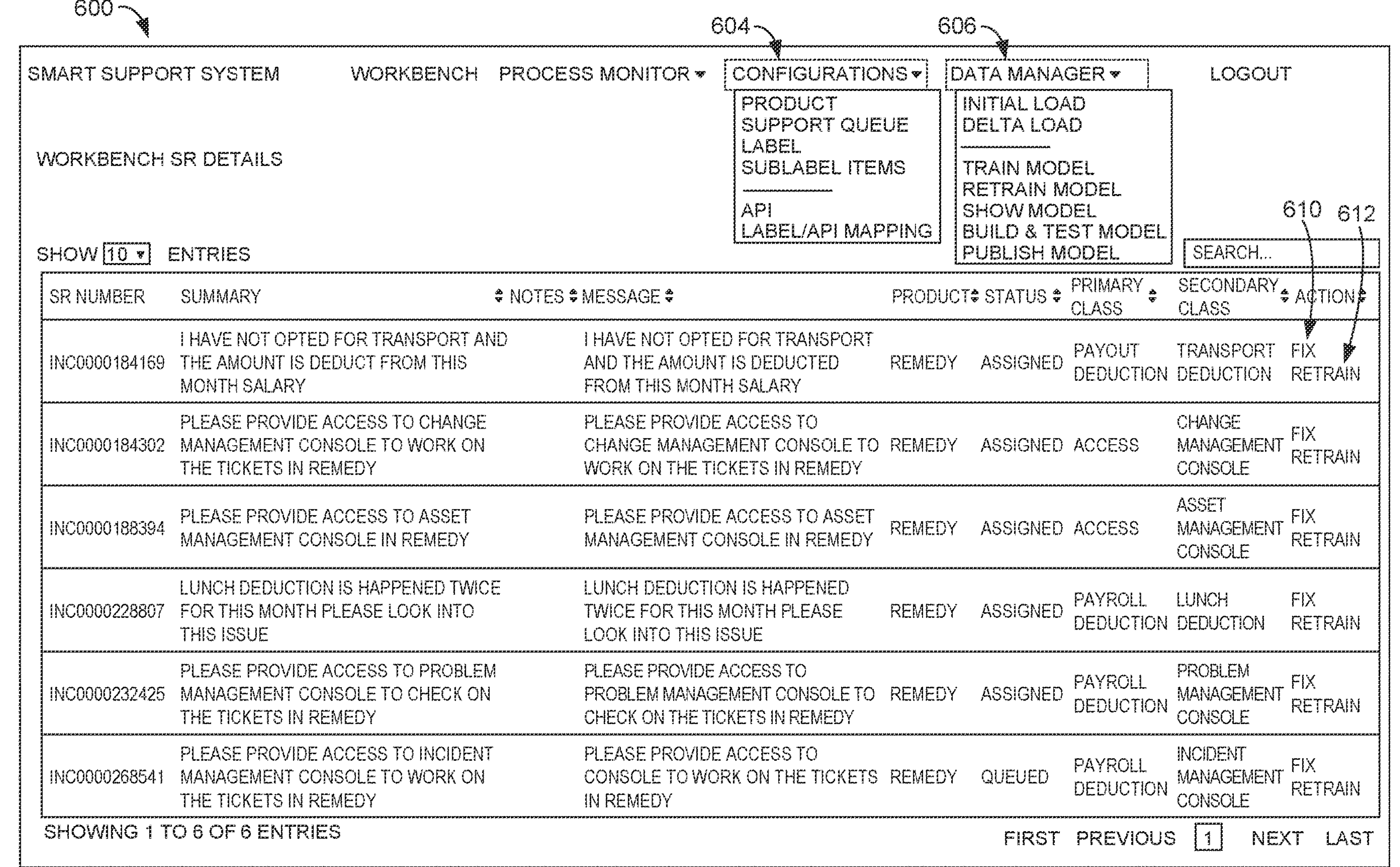

Additionally, the API may be preassigned to a classification group, or subgroup as discussed herein. In example embodiments, if the rate of success does not meet the predetermined threshold, the determined classification group or classification subgroup may be flagged for review or retraining. For example, as shown in FIG. 6A, the determined classification group or classification subgroup may be displayed by a graphical user interface in association with an icon 610 which may trigger the remedy, an icon 612 which may trigger the instance for retraining, wherein the instance is a combination of the service request information, the determined classification group, and the determined classification subgroup. In further embodiments, if the instance is flagged for retraining, an engineer may manually assign the appropriate classification group or classification subgroup. In further embodiments, the instance flagged for retraining may be reentered into the machine learning algorithm as unclassified data and rerun through the algorithm.

Figure 5:
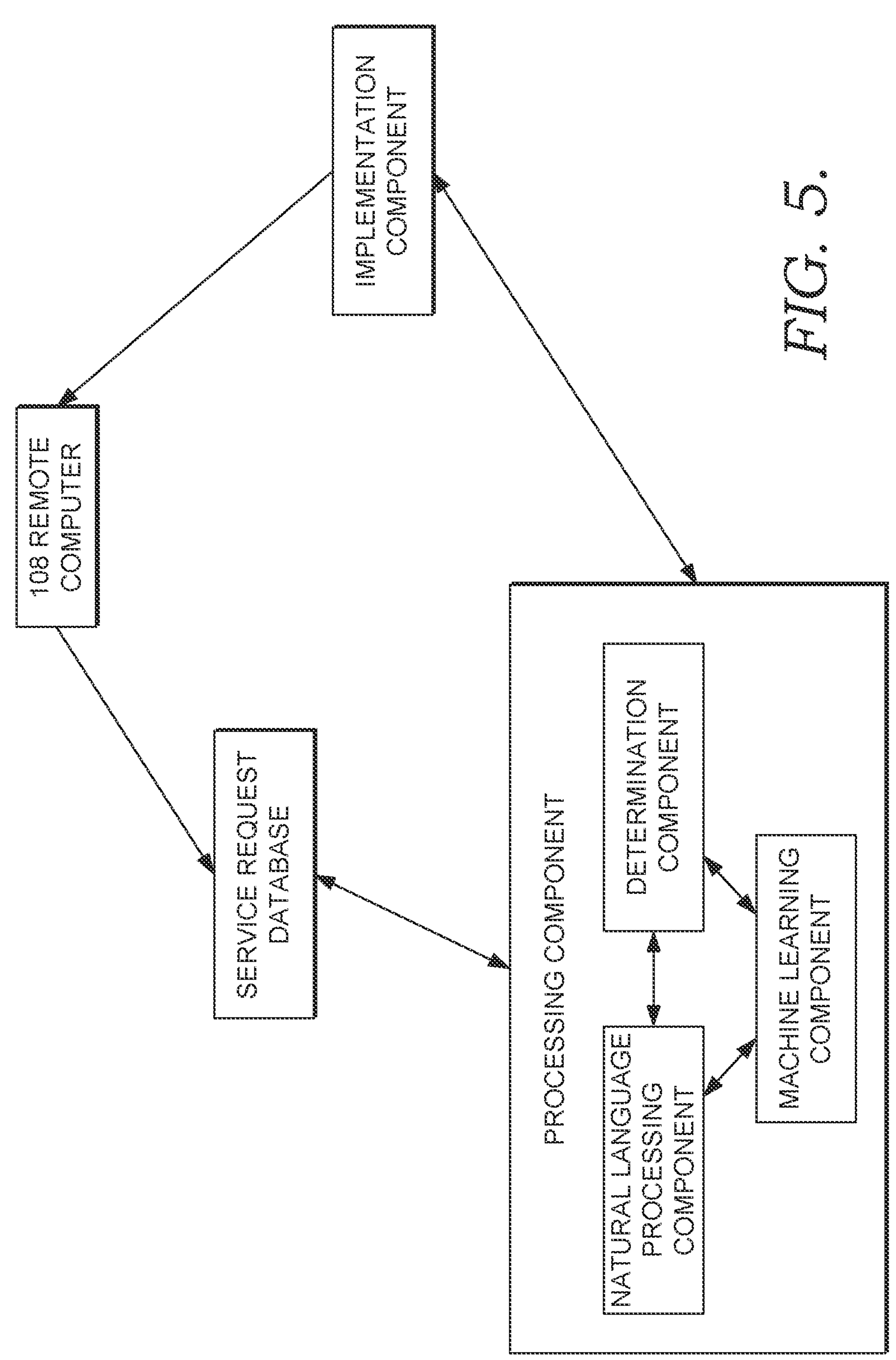
FIG. 5 illustrates a block diagram of a system for implementing intelligent remedy of system service requests, in accordance with an embodiment of the present disclosure.

Turning to FIG. 5, a block diagram of a system is displayed for implementing intelligent remedy of system service requests, in accordance with an embodiment of the present disclosure. In example embodiments, the system comprises a hardware processor configured to perform operations in response to receiving an instruction selected from a predefined native instruction set of codes, and a memory. In further embodiments, the system comprises a service request database configured to receive at least one service request related to an system from a remote computer 108. In further embodiments, the system is comprised of a processing component. In example embodiments, the processing component may be comprised of a natural language processing component configured to conduct natural language processing to determine at least one key term associated with the at least one service request. In further embodiments, the processing component is comprised of a machine learning component configured to use at least one machine learning algorithm to determine at least one classification group for the at least one service request, wherein the classification group is associated with at least one remedy. In further embodiments, the processing component is comprised of a determination component configured to determine the rate of success for the determined at least one remedy for the classification group. In further embodiments, the system comprises an implementation component configured to cause the system to implement the remedy, based on the rate of success exceeding a predetermined threshold. In further embodiments, the system may also include a display component configured to cause display on a graphical user interface, an icon displaying the at least one remedy. In example embodiments, the icon displaying the at least one remedy may be selectable by a user. In further embodiments, the display component may be configured to cause display on a graphical user interface, an icon displaying at least one service request, the classification group label, or the classification group sublabel.

Turning to FIG. 6A-6J, graphical user interfaces are provided in accordance with the aspects discussed herein. As discussed in multiple embodiments above, method may include providing a graphical user interface to an engineer, wherein the engineer may configure aspects of the method. In further embodiments, an engineer may predetermine at least classification groups, classification sub-groups, APIs, API maps, and success rate thresholds. In further embodiments, an engineer need not review information associated with computer system service requests if the determined classification group or classification subgroup has a success rate which exceeds the success rate threshold. In example embodiments, wherein the success rate of a predetermined classification group or predetermined classification subgroup is below the threshold, the method causes display of a graphical user interface associated with the instance. The engineer may then review the determined classification group or determined classification subgroup. If accurate, the engineer may select an icon associated with causing the remedy to be implemented. If inaccurate, the engineer may select an icon associated with retraining.

FIG. 6A provides a graphical user interface 600 that displays a workbench which may be interacted with by an engineer. The workbench can display multiple instances of service requests related to various matters. As can be seen in FIG. 6A, the workbench can also display various information associated with the service requests, namely, a summary of the request, the request itself, a product/application associated with the request, a primary class label associated with the determined classification group for the request, a secondary class label associated with the determined classification subgroup for the request, and icons 610 and 612. In one embodiment, the workbench provides icons 610 and 612 wherein a user can select either icon. If a determined primary class label and secondary class label are correct for a given service request, a user may select icon 610 which causes the remedy for that service request to be implemented. If a determined primary class label or secondary class label are determined to be incorrect, a user can select icon 612 which assigns the service request for retraining.

FIG. 6B provides an example embodiment a graphical user interface displaying a process view. In further embodiments, the graphical user interface of 6B displays each instance of implemented remedies in association with the related service ticket. In further embodiments, the interface of 6B also displays the ID associated with an API Map as discussed below, a status of the remedy, and the start and end time associated with the remedy.

In further embodiments, a user may select the items provided in drop down lists 604 and 606. Based on receiving a selection of "RETRAIN MODEL" as shown in FIG. 6A, the graphical user interface displays the RE-TRAIN MODEL shown in FIG. 6C. In embodiments, this user interface displays each of the service requests which have been selected for retraining. The user interface displays information related to each service ticket as well as icons for suggested class and suggested subclass. The user may use this user interface to assign new classes or subclasses to the service requests which have been selected for retraining. In an example embodiment, the user may select icon 614. By selecting this icon, the user may assign a new class or subclass, or assign a pre-existing class or subclass to the service request. Once re-assigned, the system then stores the updated class and subclass and adds the updated information to the training model as described with relation to FIG. 2.

Figure 6D:
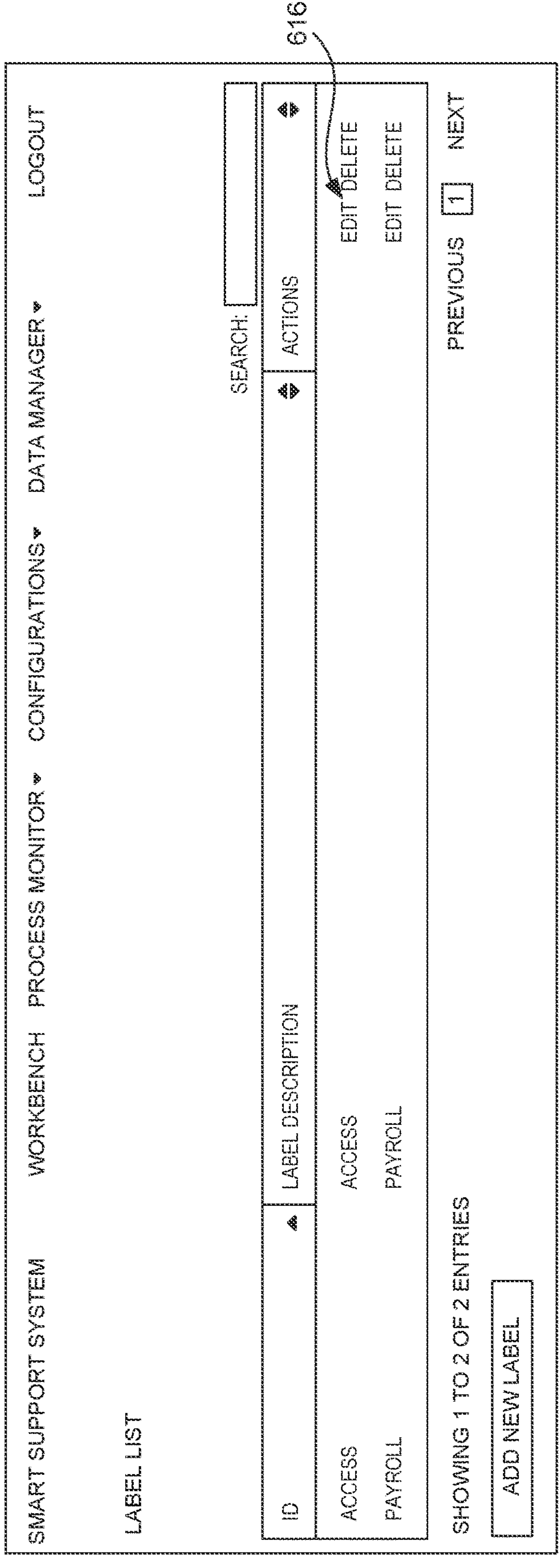
Figure 6E:
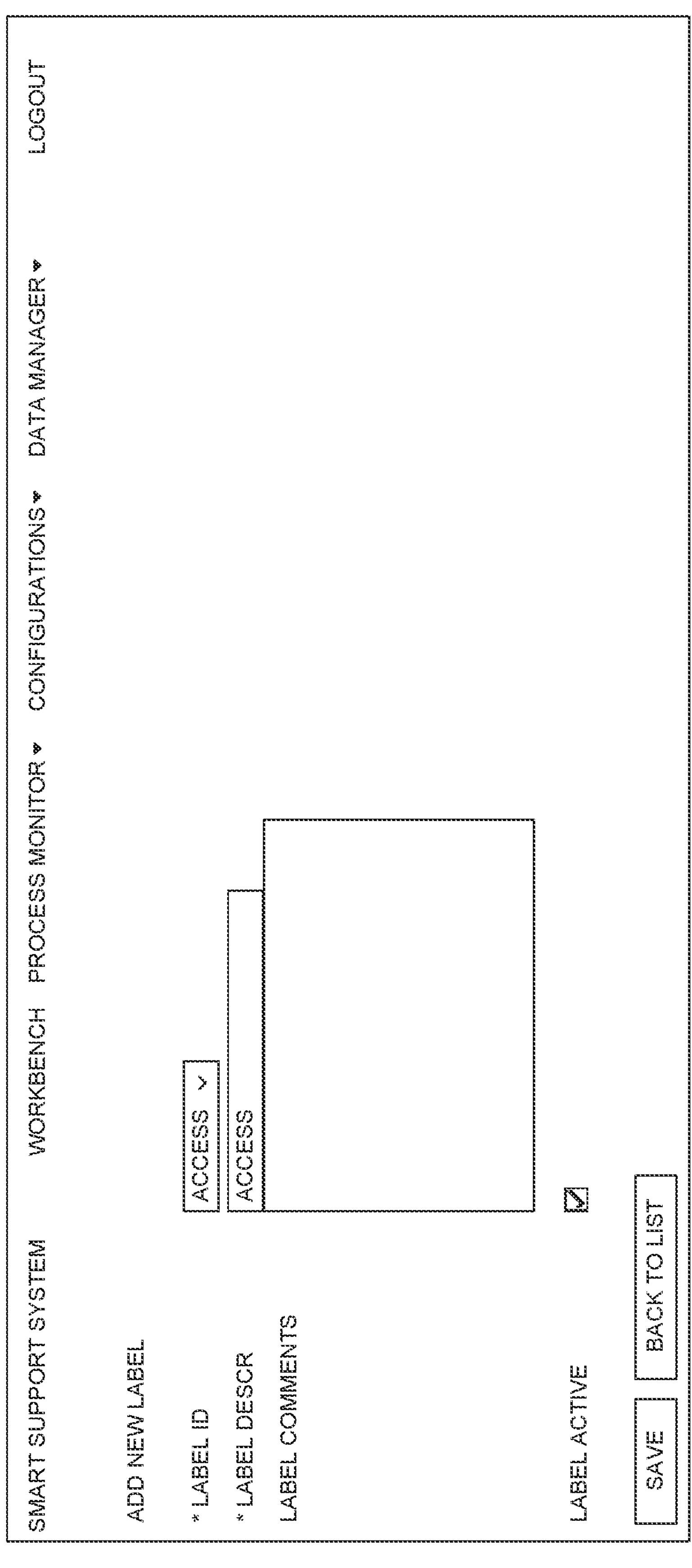

In further embodiments, a user may select LABEL in drop down list 604. In response to receiving a selection of LABEL, the graphical user interface displays the LABEL LIST as shown in FIG. 6D. In example embodiments, the graphical user interface displays the Label ID and Label Description associated with Labels which are created by the user. In further embodiments, the user may select the ADD NEW LABEL icon to create new labels for the system, or select icon 616. Based on receiving selection of icon 616, the graphical user interface displays FIG. 6E. In example embodiments, this user interface may be used to create new labels or to edit the information associated with a current label. Namely, in example embodiments, a user may edit the label description, add comments associated with the label, or create or change the Label ID. Additionally, the user may select the check box located next to LABEL ACTIVE to determine whether the system uses the created label.

Figure 6F:
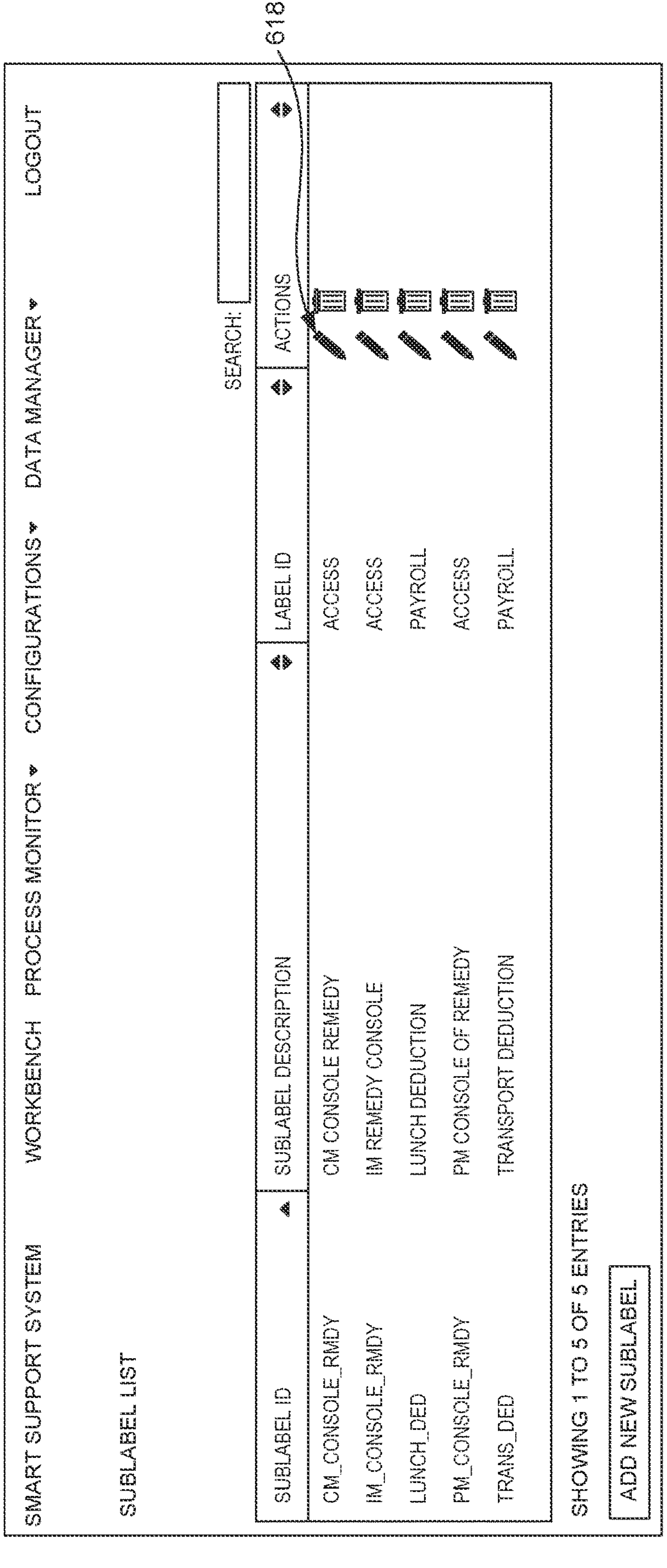
Figure 6G:
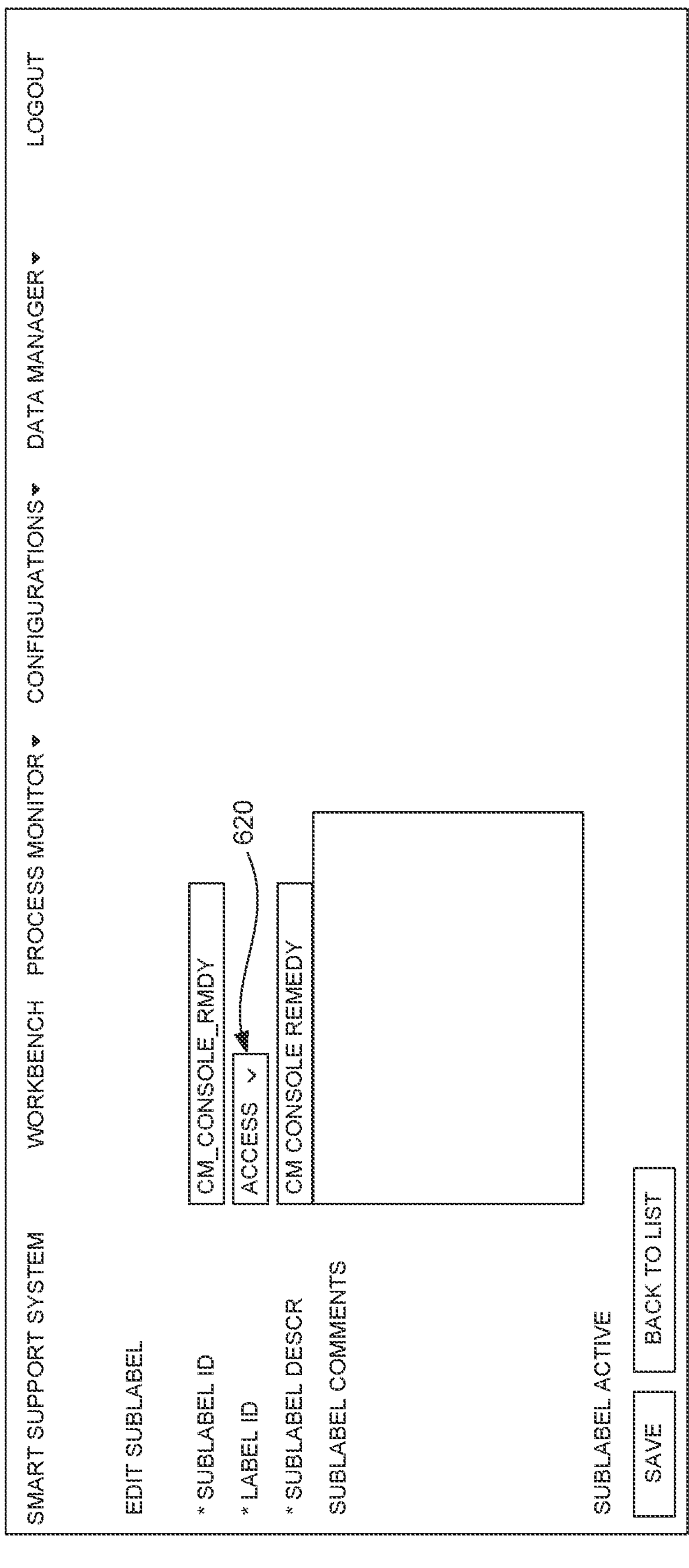

In further embodiments, a user may select SUBLABEL ITEMS in drop down list 604. In response to receiving a selection of SUBLABEL ITEMS, the graphical user interface displays the SUBLABEL LIST as shown in FIG. 6F. In example embodiments, the graphical user interface shows the sublabel ID, sublabel Description, and Label ID. Additionally, the graphical user interface displays multiple selectable icons which can be used to edit delete, or add new sublabels. In further embodiments, the user can select the edit icon 618. Based on receiving selection of the edit icon 618, the graphical user interface displays FIG. G. In example embodiments, the graphical user interface displayed in FIG. 6G allows a user to edit and customize sublabels. Specifically, the user can add a SUBLABEL ID, a SUBLABEL DESCRIPTION, and a SUBLABEL Comment. Additionally, by selecting the LABEL ID icon 620, a drop down menu is displayed with allows the user to select which label, the sublabel is associated with.

Figure 6H:
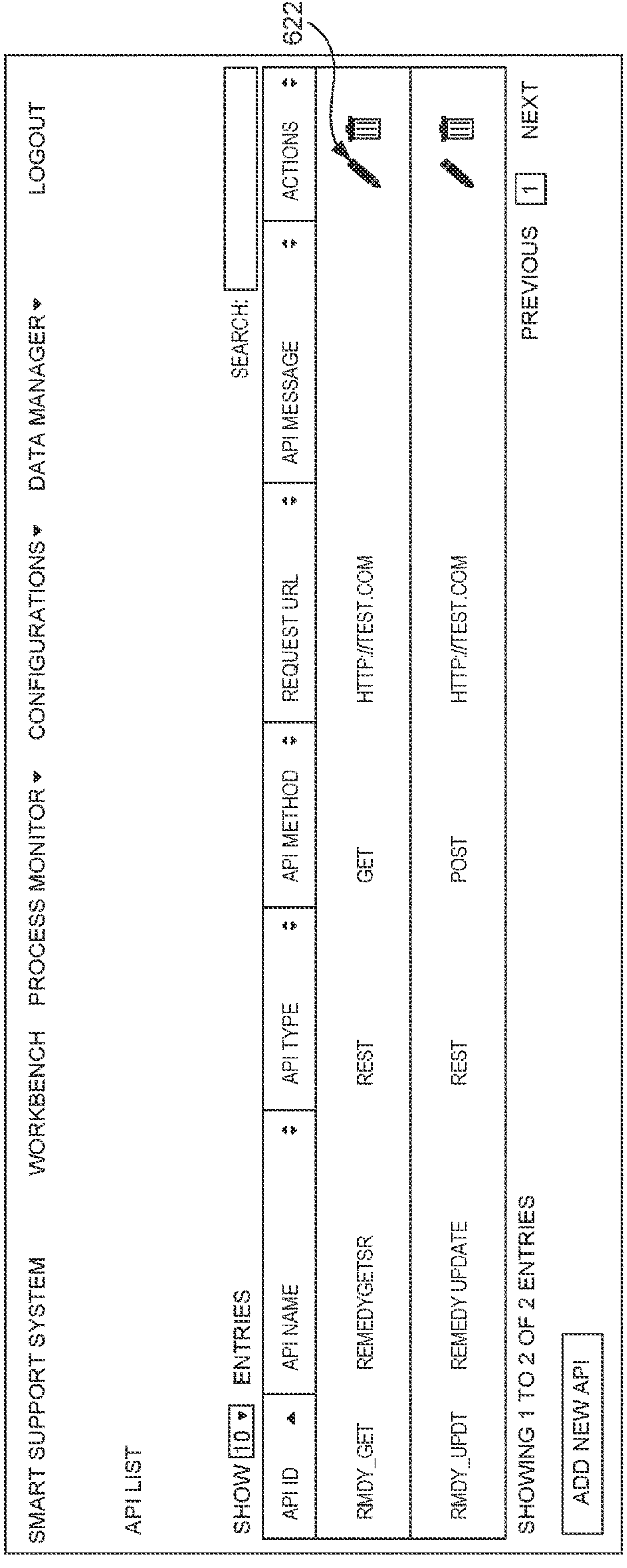
Figure 6I:
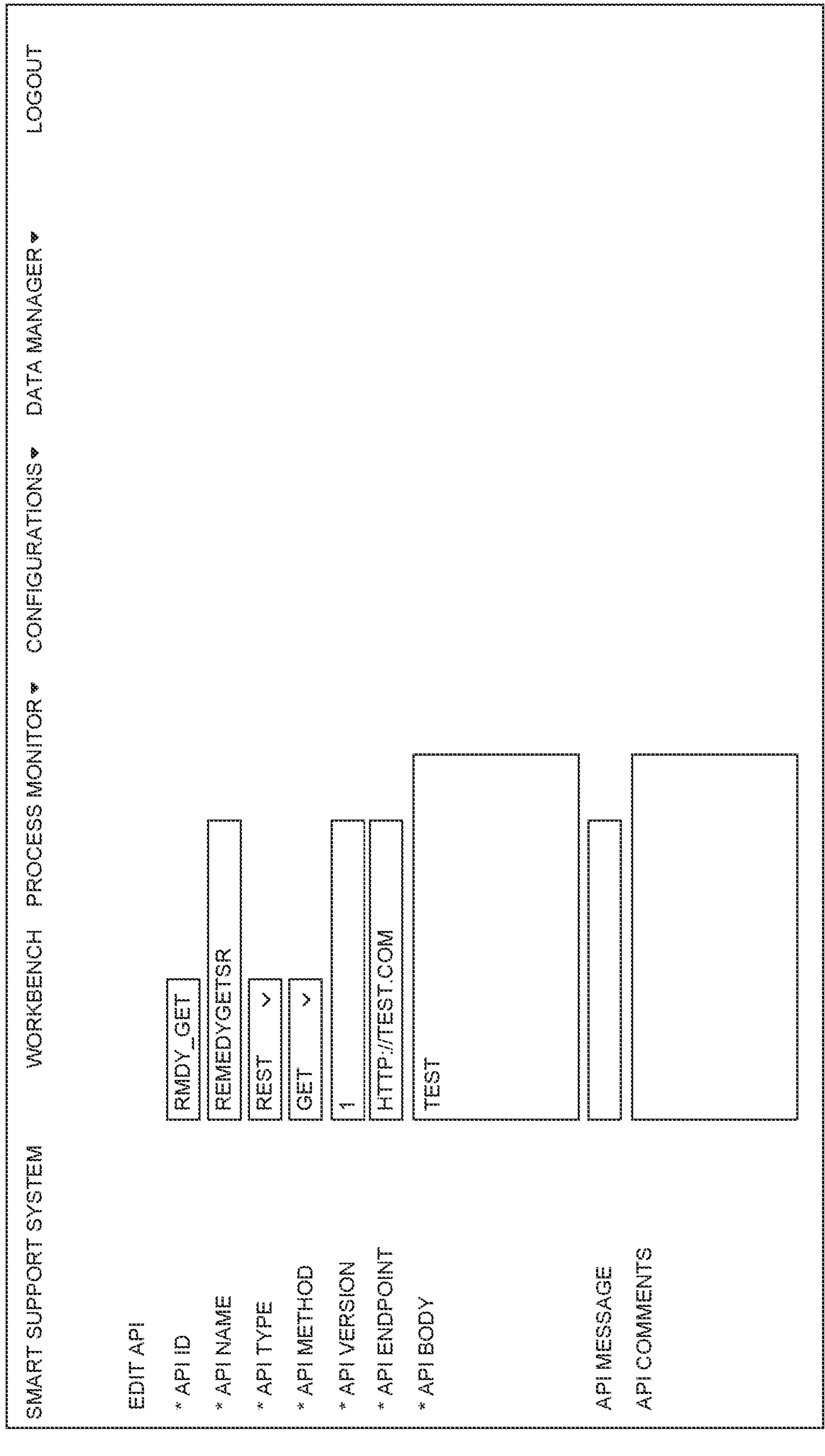

In further embodiments, a user may select API in drop down list 604. In response to receiving a selection of API, the graphical user interface displays the API LIST as shown by FIG. 6H. In example embodiments, the graphical user interface shows various information associated with Application Programming Interfaces (APIs) created by users. In embodiments, this information can be related to the API ID, API Name, the Method of the API as well as the URL from which the API may be retrieved. In example embodiments, the user may select icon 622, which when selected cause the graphical user interface to display 61. The interface displayed in 61 allows a user to edit various aspects of the selected API.

Finally, in further embodiments, a user may select LABEL/API MAPPING in drop down list 604 which causes the graphical user interface to display FIG. 6J. This interface displays various information associated with the created APIs, Labels, Sublabels, and their associated maps. From this user interface, a user may create new maps between APIs and Labels/Sublabels, or edit current API/Label. Linking the APIs to the appropriate label or sublabel through this example interface, allows the system to recognize the relationship and implement the API remedy, when the appropriate label/sublabel is determined.

The present invention has been described in relation to particular embodiments, which are intended in all respects to be illustrative rather than restrictive. Further, the present invention is not limited to these embodiments, but variations and modifications may be made without departing from the scope of the present invention.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations.

The invention claimed is:

1. A computer-implemented method for addressing and remedying problems associated with computer functionality service requests, the computer-implemented method performed by one or more hardware processors, and comprising:

receiving at least one service request (a) related to a problem and to an electronic medical record (EMR) computer system and (b) associated with a set of metadata;

inputting, via the one or more hardware processors, content associated with the at least one service request to a natural language processor (NLP), wherein inputting the content causes the NLP to output an indication of at least one key term associated with the at least one service request;

accessing, via the one or more hardware processors, a machine-learning electronic model, wherein:

(a) the machine-learning electronic model is trained based on (i) data associated with instances of terms associated with NLP based service requests and of metadata associated with the NLP based service requests and (ii) one or more decision elements associated with the instances, and (b) applying the machine-learning electronic model to data associated with items including the at least one key term and with the set of metadata generates information indicating at least one classification group and classification subgroup for the at least one service request;

automatically determining, by the one or more hardware processors, a rate of success associated with at least one remedy for the at least one classification group and classification subgroup;

in response to the rate of success associated with the at least one remedy exceeding a threshold, causing the at least one remedy to be implemented in the EMR computer system;

determining whether or not the at least one remedy was successful for the problem; and in response to determining that the at least one remedy was successful for the problem, re-entering information reflecting that the at least one remedy was successful for the problem into the machine-learning electronic model to retrain the machine-learning electronic model, wherein the rate of success is automatically determined based on a number of accurately classified groups and subgroups re-entered into the machine-learning electronic model.

2. The computer-implemented method of claim 1, wherein the at least one classification group is comprised of an EMR functionality issue.

3. The computer-implemented method of claim 1, wherein implementing the at least one remedy for the problem comprises:

determining that a server associated with the EMR computer system is down; and based on determining that the server associated with the EMR computer system is down, causing a reboot of the server.

4. The computer-implemented method of claim 1, further comprising:

determining that the at least one remedy was not successful for the problem; and based on determining that the at least one remedy was not successful for the problem, flagging the at least one classification group for retraining via a machine learning algorithm.

5. One or more non-transitory media having instructions that, when executed by one or more hardware processors, cause the one or more hardware processors to perform a plurality of operations for addressing and remedying problems associated with computer functionality service requests, the operations comprising:

receiving at least one service request (a) related to a problem and to an electronic medical record (EMR) computer system and (b) associated with a set of metadata;

inputting, via the one or more hardware processors, content associated with the at least one service request to a natural language processor (NLP), wherein inputting the content causes the NLP to output an indication of at least one key term associated with the at least one service request;

accessing, via the one or more hardware processors, a machine-learning electronic model, wherein:

(a) the machine-learning electronic model is trained based on (i) data associated with instances of terms associated with NLP based service requests and of metadata associated with the NLP based service requests and (ii) one or more decision elements associated with the instances, and (b) applying the machine-learning electronic model to data associated with items including the at least one key term and with the set of metadata generates information indicating at least one classification group and classification subgroup for the at least one service request;

automatically determining, by the one or more hardware processors, a rate of success associated with at least one remedy for the at least one classification group and classification subgroup;

in response to the rate of success associated with the at least one remedy exceeding a threshold, causing the at least one remedy to be implemented in the EMR computer system;

determining whether or not the at least one remedy was successful for the problem; and in response to determining that the at least one remedy was successful for the problem, re-entering information reflecting that the at least one remedy was successful for the problem into the machine-learning electronic model to retrain the machine-learning electronic model, wherein the rate of success is automatically determined based on a number of accurately classified groups and subgroups re-entered into the machine-learning electronic model.

6. The one or more non-transitory media of claim 5, wherein the at least one classification group is associated with at least one application programming interface, and wherein the at least one application programming interface is configured to implement the at least one remedy for the problem in the EMR computer system.

7. The one or more non-transitory media of claim 5, wherein at least one of the operations is performed using a distributed electronic agent architecture that is associated with a geographically distributed electronic memory.

8. The one or more non-transitory media of claim 5, wherein one or more of the operations are performed using a geographically distributed medical-information computing system associated with at least one network coupled electronic memory.

9. The one or more non-transitory media of claim 5, wherein at least one of the operations is performed using a plurality of electronic agents that are associated with a distributed electronic memory of a health care computing system.

10. The one or more non-transitory media of claim 5, wherein the one or more hardware processors comprise a distributed adaptive agent that includes a neural network and/or is associated with a distributed memory of an electronic records computing system.

11. The one or more non-transitory media of claim 5, wherein the determining of the at least one key term, the determining of the at least one classification group, the applying of the machine-learning electronic model to the data associated with the items, the automatic determining, and the causing of the at least one remedy to be implemented in the EMR computer system occur automatically without user input.

12. The one or more non-transitory media of claim 5, wherein the operations further comprise:

detecting that the at least one remedy was successful for the problem; and based on the detecting, storing information associated with the at least one remedy, the at least one service request, and the at least one classification group, in a database associated with a machine learning component.

13. The one or more non-transitory media of claim 5, wherein causing the at least one remedy to be implemented comprises:

Identifying, by the one or more hardware processors and based on the metadata and on the at least one classification group and classification subgroup, an EMR functionality issue; and initiating, by the one or more hardware processors and based on the identifying, an action that cures the EMR functionality issue.

14. The one or more non-transitory media of claim 5, wherein causing the at least one remedy to be implemented comprises:

accessing, by the one or more hardware processors, a plurality of application programming interface (API) mappings stored at the EMR computer system;

selecting an API set of data, from multiple sets of data stored with the plurality of API mappings, based on the metadata and the at least one classification group and classification subgroup; and initiating, by the one or more hardware processors and based on the selecting, an API call using the API set of data.

15. The one or more non-transitory media of claim 14, wherein initiating the API call: uses a particular communication address and protocol, identified by the API set of data, to plug into an API device associated with a cloud-based service system; and implements, via the cloud-based service system, the at least one remedy at the EMR computer system to remedy an EMR functionality issue.

16. A system having one or more hardware processors configured to perform a plurality of operations for addressing and remedying problems associated with computer functionality service requests, the operations comprising:

receiving at least one service request (a) related to a problem and to an electronic medical record (EMR) computer system and (b) associated with a set of metadata;

inputting, via the one or more hardware processors, content associated with the at least one service request to a natural language processor (NLP), wherein inputting the content causes the NLP to output an indication of at least one key term associated with the at least one service request;

accessing, via the one or more hardware processors, a machine-learning electronic model, wherein:

(a) the machine-learning electronic model is trained based on (i) data associated with instances of terms associated with NLP based service requests and of metadata associated with the NLP based service requests and (ii) one or more decision elements associated with the instances, and (b) applying the machine-learning electronic model to data associated with items including the at least one key term and with the set of metadata generates information indicating at least one classification group and classification subgroup for the at least one service request;

automatically determining, by the one or more hardware processors, a rate of success associated with at least one remedy for the at least one classification group and classification subgroup;

in response to the rate of success associated with the at least one remedy exceeding a threshold, causing the at least one remedy to be implemented in the EMR computer system;

determining whether or not the at least one remedy was successful for the problem; and in response to determining that the at least one remedy was successful for the problem, re-entering information reflecting that the at least one remedy was successful for the problem into the machine-learning electronic model to retrain the machine-learning electronic model, wherein the rate of success is automatically determined based on a number of accurately classified groups and subgroups re-entered into the machine-learning electronic model.

17. The system of claim 16, wherein the at least one classification group includes predetermined information associated with an input by a user device.

18. The system of claim 16, wherein the at least one classification group includes at least one classification subgroup.

19. The system of claim 16, wherein the machine-learning electronic model includes a random forest algorithm.

20. The system of claim 16, further comprising a display component configured to display on a graphical user interface an icon indicating the at least one remedy for the problem.

* * * * *